United States Patent
Jaax et al.

(10) Patent No.: US 8,515,542 B2
(45) Date of Patent: Aug. 20, 2013

(54) TREATMENT OF OBESITY AND/OR TYPE II DIABETES BY STIMULATION OF THE PITUITARY GLAND

(75) Inventors: Kristen N. Jaax, Santa Clarita, CA (US); Allison M. Foster, Valencia, CA (US); Todd K. Whitehurst, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 92 days.

(21) Appl. No.: 13/098,907

(22) Filed: May 2, 2011

(65) Prior Publication Data

US 2011/0238035 A1    Sep. 29, 2011

Related U.S. Application Data

(63) Continuation of application No. 12/102,582, filed on Apr. 14, 2008, now Pat. No. 7,945,323.

(60) Provisional application No. 60/923,369, filed on Apr. 13, 2007.

(51) Int. Cl.
*A61N 1/36* (2006.01)

(52) U.S. Cl.
USPC .......................................................... 607/45

(58) Field of Classification Search
None
See application file for complete search history.

(56) References Cited

U.S. PATENT DOCUMENTS

| | | | |
|---|---|---|---|
| 7,200,443 B2 * | 4/2007 | Faul | 607/40 |
| 7,440,806 B1 * | 10/2008 | Whitehurst et al. | 607/45 |
| 7,493,171 B1 * | 2/2009 | Whitehurst et al. | 607/58 |
| 7,561,918 B2 * | 7/2009 | Armstrong et al. | 607/39 |
| 7,623,924 B2 * | 11/2009 | Narciso, Jr. | 607/39 |
| 2006/0036293 A1 * | 2/2006 | Whitehurst et al. | 607/40 |

* cited by examiner

*Primary Examiner* — Kennedy Schaetzle
(74) *Attorney, Agent, or Firm* — Vista IP Law Group LLP (57) ABSTRACT

Methods of treating obesity and/or type II diabetes include applying at least one stimulus to the pituitary gland of a patient with an implanted stimulator in accordance with one or more stimulation parameters. The at least one stimulus is configured to treat obesity and/or type II diabetes. Systems for treating obesity and/or type II diabetes include a stimulator configured to apply at least one stimulus to the pituitary gland of a patient in accordance with one or more stimulation parameters. The at least one stimulus is configured to treat obesity and/or type II diabetes.

16 Claims, 11 Drawing Sheets

TREATMENT OF OBESITY AND/OR TYPE II DIABETES BY STIMULATION OF THE PITUITARY GLAND

RELATED APPLICATIONS

The present application is a continuation of co-pending U.S. application Ser. No. 12/102,582, filed Apr. 14, 2008, which claims priority under 35 U.S.C. §119(e) to U.S. Provisional Patent Application Ser. No. 60/923,369 by Kristen N. Jaax et al., filed on Apr. 13, 2007, and entitled "Treatment of Obesity and/or Type II Diabetes by Stimulation of the Pituitary Gland," the contents of which are hereby incorporated by reference in their entirety.

BACKGROUND

Obesity is one of the most prevalent public heath problems in the United States and affects millions of Americans. An especially severe type of obesity, called morbid obesity, is characterized by a body mass index greater than or equal to 40 or a body weight that is 100 or more pounds over normal weight.

Recent studies have shown that over 300,000 deaths are caused by obesity in the United States each year. In addition, millions suffer broken bones, social isolation, arthritis, sleep apnea, asphyxiation, heart attacks, diabetes, and other medical conditions that are caused or exacerbated by obesity.

Patients suffering from obesity have very limited treatment options. For example, drugs such as sibutramine, diethylproprion, mazindol, phentermine, phenylpropanolamine, and orlistat are often used to treat obesity. However, these drugs are effective only for short-term use and have many adverse side-effects.

Another treatment option for obesity is surgery. For example, a procedure known as "stomach stapling" reduces the effective size of the stomach and the length of the nutrient-absorbing small intestine to treat obesity. However, surgery is highly invasive and is often associated with both acute and chronic complications including, but not limited to, infection, digestive problems, and deficiency in essential nutrients.

Obesity is intricately related to diabetes, in particular type II diabetes. Type II diabetes is characterized by body tissue resistance to insulin activity. Many studies suggest that obesity increase a person's chances of developing type II diabetes.

Likewise, type II diabetes increases a person's propensity to become obese. As cells within the body become less responsive to the actions of insulin, the pancreas is forced to continuously produce more insulin to drive glucose into cells. The excess insulin that is produced as a result of insulin resistance increases the storage of body fat and thereby increases a person's propensity to become obese.

Patients suffering from type II diabetes also have limited treatment options. Type II diabetes is typically controlled with diet, weight loss, exercise, and oral medications. More than half of all people with type II diabetes require insulin to control their blood sugar levels at some point in the course of their illness. However, these treatment options are made difficult when type II diabetes is accompanied by obesity.

SUMMARY

Methods of treating obesity and/or type II diabetes include applying at least one stimulus to the pituitary gland of a patient with an implanted stimulator in accordance with one or more stimulation parameters. The at least one stimulus is configured to treat obesity and/or type II diabetes.

Systems for treating obesity and/or type II diabetes include a stimulator configured to apply at least one stimulus to the pituitary gland of a patient in accordance with one or more stimulation parameters. The at least one stimulus is configured to treat obesity and/or type II diabetes.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for treating obesity and/or type II diabetes are described herein. An implanted stimulator is configured to apply at least one stimulus to a stimulation site within a patient in accordance with one or more stimulation parameters. The stimulus is configured to treat obesity and/or type II diabetes and may include electrical stimulation, drug stimulation, gene infusion, chemical stimulation, thermal stimulation, electromagnetic stimulation, mechanical stimulation, and/or any other suitable stimulation. As used herein, and in the appended claims, "treating" obesity and/or type II diabetes refers to any amelioration of one or more causes and/or one or more symptoms of obesity and/or type II diabetes. For example, treating obesity and/or type II diabetes as described herein may include, without being limited to, preventing weight gain, regulating gastrointestinal activity, creating a sensation of fullness such that the patient eats less, and/or reducing a sensation of hunger within the patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
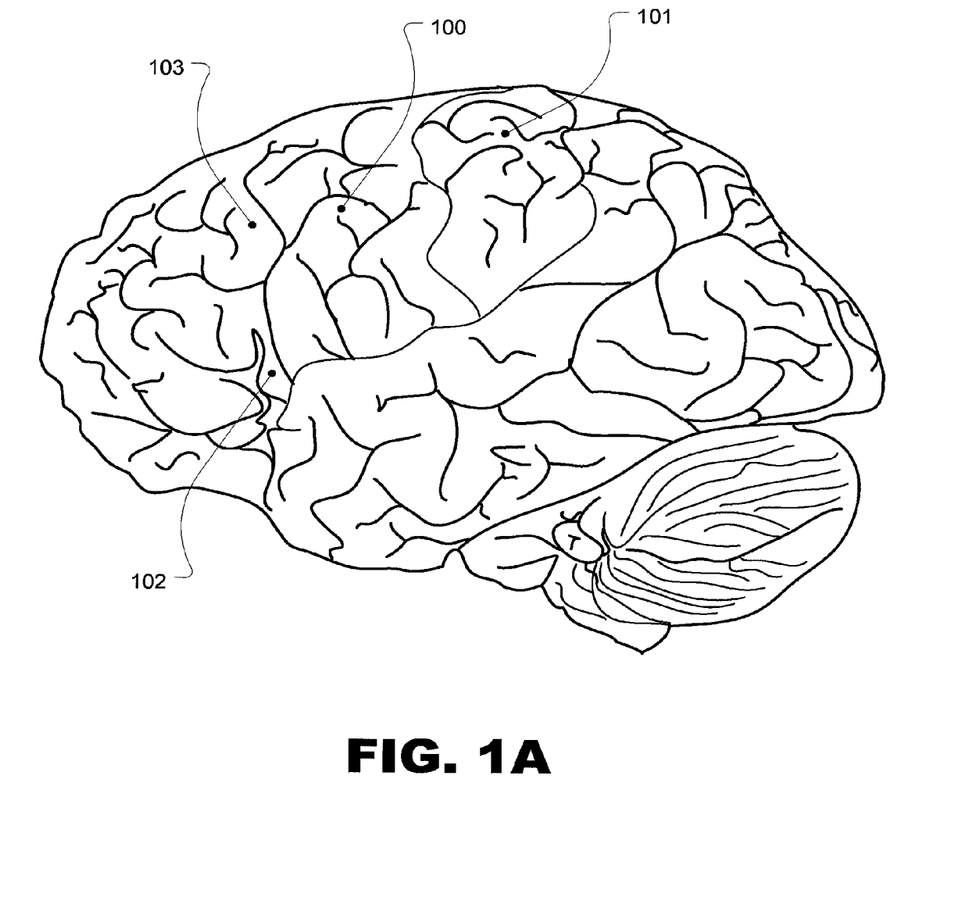
FIG. 1A depicts the lateral surface of the brain.

Before discussing the present methods and systems for treating obesity and/or type II diabetes, a brief overview of the brain will be given. FIG. 1A depicts the lateral surface of the brain. As shown in FIG. 1A, the primary motor cortex 100 is located on the lateral surface of the brain. Activity within the primary motor cortex 100 influences motor movements. Also shown in FIG. 1A are the somatosensory cortex 101, premotor cortex 102, and supplementary motor cortex 103. These structures are also involved in controlling motor movements.

Figure 1B:
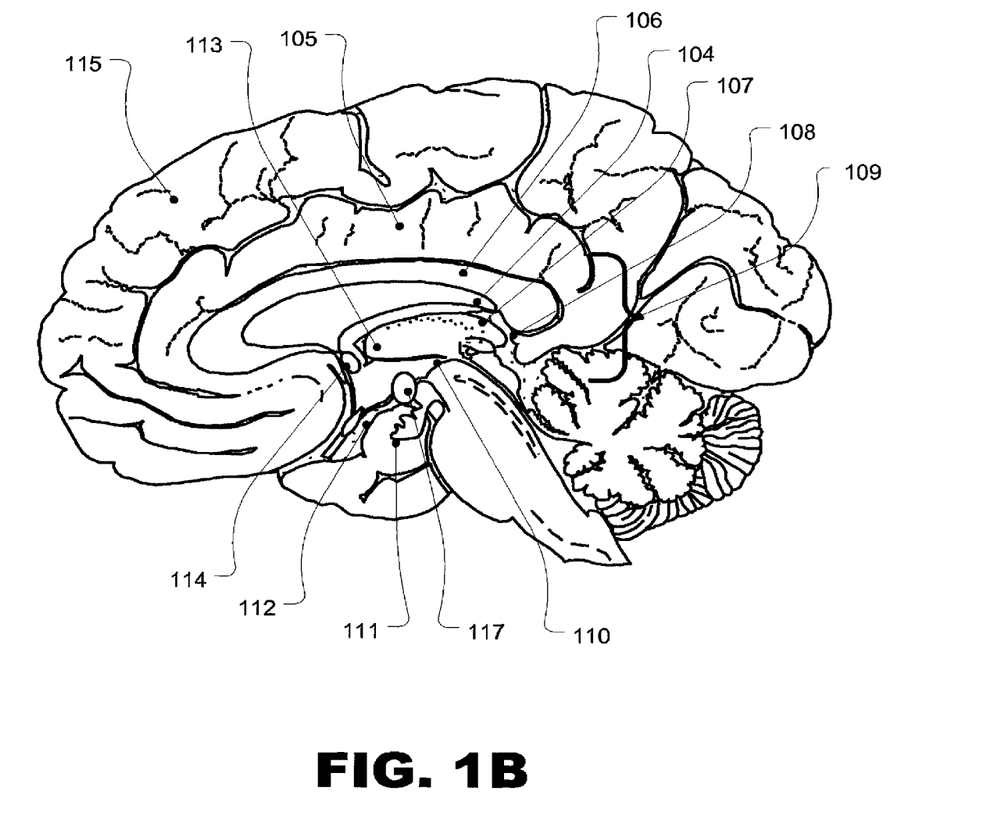
FIG. 1B depicts, in perspective view, the thalamus and various structures of the brain that make up the limbic system.

FIG. 1B depicts, in perspective view, the thalamus 104 and various structures of the brain that make up the limbic system. The thalamus 104 helps process information from the senses and relays such information to other parts of the brain. Located beneath the thalamus is the hypothalamus (not shown). The hypothalamus regulates many body functions, including appetite and body temperature.

The limbic system shown in FIG. 1B includes, but is not limited to, several subcortical structures located around the thalamus 104. Exemplary structures of the limbic system include the cingulate gyrus 105, corpus collosum 106, stria terminalis 107, caudate nucleus 108, basal ganglia 109, hippocampus 110, enterorhinal cortex 111, amygdala 112, mammillary body 113, medial septal nucleus 114, prefrontal cortex 115, and fornix 116. These structures are involved with emotion, learning, and memory.

FIG. 1B also shows the pituitary gland 117. The pituitary gland 117 is a small gland located at the base of the brain that secretes several different hormones involved in key metabolic processes throughout the body. The pituitary gland 117 also controls a number of endocrine systems in the body. Imbalances in the pituitary gland 117 can increase the amount of cortisol that is produced by the adrenal glands. It has been discovered that this overproduction of cortisol can lead to overeating and/or increased fat production in the body. Hence, a malfunction of the pituitary gland 117 may lead to obesity and/or type II diabetes.

It is believed that applying a stimulus to one or more stimulation sites within the brain may be useful in treating obesity and/or type II diabetes. For example, it is believed that applying a stimulus to the pituitary gland may be useful in treating obesity and/or type II diabetes. As mentioned, "treating" obesity and/or type II diabetes refers to any amelioration of one or more causes and/or symptoms of obesity and/or type II diabetes. By treating obesity and/or type II diabetes, the methods and systems described herein may also be used to treat other diseases or conditions that are sequelae of obesity and/or type II diabetes such as, but not limited to, obstructive sleep apnea (OSA), hyperlipidemia, infertility, hypertension, metabolic syndrome, osteoarthritis, gastroesophageal reflux disease (GERD), coronary artery disease, cholelithiasis, hypertriglyceridemia, heart failure, and gout.

Consequently, a stimulator may be implanted within a patient to deliver a stimulus to one or more stimulation sites within the patient in order to treat obesity and/or type II diabetes. The stimulus may include an electrical stimulation current, one or more drugs or other chemical stimulation, thermal stimulation, electromagnetic stimulation, mechanical stimulation, and/or any other suitable stimulation.

The one or more stimulation sites referred to herein, and in the appended claims, may include, but are not limited to, any one or more of the locations within the brain as described above. For example, the stimulation site may include, but is not limited to, the pituitary gland.

As used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, and/or any other suitable stimulation at a stimulation site to treat obesity and/or type II diabetes. Thus, the term "stimulator" includes, but is not limited to, a microstimulator, implantable pulse generator (IPG), spinal cord stimulator (SCS), system control unit, deep brain stimulator, drug pump, or similar device.

Figure 2:
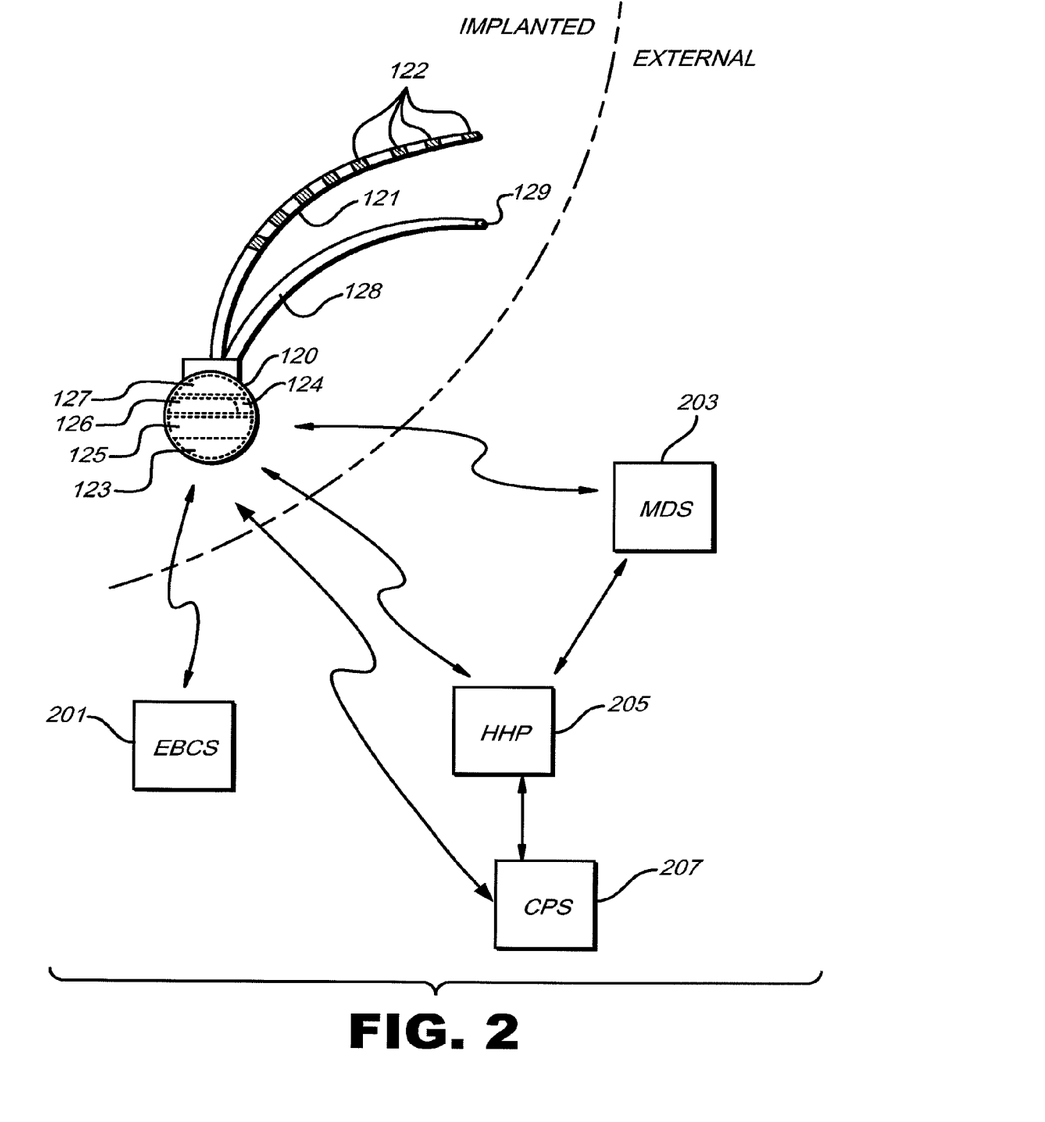
FIG. 2 illustrates an exemplary stimulator that may be used to apply a stimulus to a stimulation site within a patient to treat obesity and/or type II diabetes according to principles described herein.

To facilitate an understanding of the methods of treating obesity and/or type II diabetes with an implanted stimulator, a more detailed description of a stimulator and its operation will now be given with reference to the figures. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application. In some alternative examples, as will be described in more detail below, the stimulator 120 may be leadless.

As illustrated in FIG. 2, the stimulator 120 includes a number of components. For example, the stimulator 120 may include a power source 123, coil 124, electrical circuitry 125, a programmable memory unit 126, and/or a pump 127. It will be recognized that the stimulator 120 may include additional and/or alternative components as best serves a particular application.

The power source 123 is configured to output voltage used to supply the various components within the stimulator 120 with power and/or to generate the power used for electrical stimulation. The power source 123 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 123 may be recharged using an external charging system. One type of rechargeable power supply that may be used is described in U.S. Pat. No. 6,596,439, which is incorporated herein by reference in its entirety. Other battery construction techniques that may be used to make the power source 123 include those shown, e.g., in U.S. Pat. Nos. 6,280,873; 6,458,171; 6,605,383; and 6,607,843, all of which are incorporated herein by reference in their respective entireties.

The stimulator 120 may also include a coil 124 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 123.

The stimulator 120 may also include electrical circuitry 125 configured to generate the electrical stimulation current that is delivered to a stimulation site via one or more of the electrodes 122. For example, the electrical circuitry 125 may include one or more processors, capacitors, integrated circuits, resistors, coils, and/or any other component configured to generate electrical stimulation current.

The exemplary stimulator 120 shown in FIG. 2 may additionally or alternatively be configured to provide drug stimulation to a patient by applying one or more drugs at a stimulation site within the patient. To this end, a pump 127 may also be included within the stimulator 120. The pump 127 may be configured to store and dispense one or more drugs, for example, through a catheter 128 that is coupled to the stimulator 120. The catheter 128 may be coupled at a proximal end to the stimulator 120 and may include an infusion outlet 129 for infusing dosages of the one or more drugs at the stimulation site. In some embodiments, the stimulator 120 may include multiple catheters 128 and/or pumps for storing and infusing dosages of the one or more drugs at the stimulation site.

The one or more drugs applied by the stimulator 120 may include any drug or other substance configured to treat obesity and/or type II diabetes. For example, the one or more drugs that may be applied to a stimulation site to treat obesity and/or type II diabetes may have an excitatory effect on the stimulation site. Additionally or alternatively, the one or more drugs may have an inhibitory effect on the stimulation site in order to treat obesity and/or type II diabetes. Exemplary excitatory drugs that may be applied to a stimulation site to treat obesity and/or type II diabetes include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat obesity and/or type II diabetes include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat obesity and/or type II diabetes include, but are not limited to, at least one or more of the following substances: capsaicin, a neurotoxic substance, neurotrophic factors (e.g., brain derived neotrophic factors (BDNF) and glial cell line derived neurotrophic factors (GDNF)), steroids, antibiotics, analgesics, gastrin, one or more peptides (e.g., neuropeptide Y), cholecystokinin (CCK). Capsaicin and neurotoxic substances can act as excitotoxic agents and may be placed on the olfactory epithelium to decrease perception of scents. Neurotrophic factors, steroids, and antibiotics have been shown to increase efficacy of drug infusion, reduce fibrosis, and/or prevent infection. Gastrin, peptides, and cholecystokinin modulate intake of food.

Any of the drugs listed above, alone or in combination, or other drugs or combinations of drugs developed or shown to treat obesity and/or type II diabetes or their respective symptoms may be applied to the stimulation site to treat obesity and/or type II diabetes. In some embodiments, the one or more drugs are infused chronically into the stimulation site. Additionally or alternatively, the one or more drugs may be infused acutely into the stimulation site in response to a biological signal or a sensed need for the one or more drugs.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus.

Specific stimulation parameters may have different effects on different types, causes, or symptoms of obesity and/or type II diabetes. Thus, in some examples, the stimulation parameters may be adjusted at any time throughout the treatment course as best serves the particular patient being treated. It will be recognized that any of the characteristics of the stimulation current, including, but not limited to, the pulse shape, amplitude, pulse width, frequency, burst pattern (e.g., continuous or intermittent), duty cycle or burst repeat interval, ramp on time, and ramp off time may be adjusted throughout the course of treatment as best serves a particular application.

To illustrate, a baseline set of stimulation parameters may initially be set to begin treatment of obesity and/or type II diabetes. These baseline values may be adjusted throughout the course of treatment in response to patient feedback or sensed indicators of obesity and/or type II diabetes. Additionally or alternatively, the patient and/or clinician may adjust the stimulation parameters at any time to prevent accommodation, collateral stimulation, and/or ineffectiveness.

An exemplary baseline set of stimulation parameters that may be used to initially define stimulation current that is used to treat obesity and/or type II diabetes includes, but is not limited to the stimulation parameters shown in Table 1. It will be recognized that the baseline set of stimulation parameters shown in Table 1 may vary depending on the particular patient being treated and that additional or alternative stimulation parameters may be defined.

TABLE 1

Exemplary Baseline Stimulation Parameters

| Pulse width | 10 microseconds (μsec) |
| --- | --- |
| Frequency | 30 Hz |
| Burst pattern | Continuous |
| Amplitude | 0.1 milliamps (mA) |

Hence, as shown in Table 1, a continuous stimulation current having a pulse width of 10 μsec, a frequency of 30 Hz, and an amplitude of 0.1 mA may be initially applied to a stimulation site within the patient (e.g., the pituitary gland) in order to treat obesity and/or type II diabetes. The pulse width, frequency, and amplitude may initially have relatively small values so as to avoid muscle spasms, nerve damage, or discomfort.

In some examples, these baseline parameters may be determined in the initial fitting session and may depend on the electrode placement (e.g., how proximal they are to the stimulation site), local impedance (which may be affected by scar tissue, etc.), and patient variability. The clinician or other programmer may make subtle, iterative adjustments to any of the stimulation parameters in response to real-time feedback from the patient.

After a predetermined length of time (e.g., one or more weeks, months, or years) of treatment or as the need may arise, the patient may be evaluated to determine whether the stimulation parameters need to be adjusted and/or whether the additional stimulation is needed in order to treat obesity and/or type II diabetes. In some examples, if the patient no longer exhibits any symptoms of obesity and/or type II diabetes, the stimulation may be terminated. Alternatively, if it is determined that the patient needs further treatment, the stimulation may continue in accordance with the same set of stimulation parameters or in accordance with a newly defined set of stimulation parameters. For example, the stimulation parameters may be adjusted from the exemplary baseline stimulation parameters described previously in connection with Table 1 to have the exemplary values within the ranges shown in Table 2:

TABLE 2

Exemplary Adjusted Stimulation Parameters

| Pulse width | 5 μsec |
| --- | --- |
| Frequency | 120 Hz |
| Burst pattern | Continuous |
| Amplitude | 0.2 mA |

As shown in Table 2, the pulse width, frequency, and/or amplitude may be adjusted so that the stimulation current more effectively treats obesity and/or type II diabetes. For example, the pulse width, frequency, and/or amplitude may be adjusted to more suitable values. It will be recognized that the values shown in Table 2 are merely illustrative and that they may vary as may serve a particular application. It will also be recognized that any other stimulation parameter (e.g., one or more of the drug stimulation parameters) may additionally or alternatively be adjusted in order to more effectively treat obesity and/or type II diabetes.

In some examples, the stimulation parameters may be configured to provide monopolar electrical stimulation. For example, an external case of the stimulator 120 may be used as an indifferent electrode. In other embodiments, the stimulation parameters may be configured to provide bipolar electrical stimulation (e.g., one of the electrodes 122 may be used as an indifferent electrode). Different stimulation parameters may have different effects on neural or other tissue. Therefore, parameters may be chosen to target specific neural or other tissue populations and/or exclude others in order to achieve a desired therapeutic effect. Additionally, the stimulation parameters may provide for current steering between electrodes 122 such that one or more specific stimulation sites may be targeted.

In some examples, it may be desirable to increase excitement of a stimulation site in order to treat obesity and/or type II diabetes. To facilitate increased excitement of a stimulation site, the stimulation parameters may be adjusted such that the stimulator 120 applies a stimulation current having a relatively low frequency (e.g., less than 100 Hz) to the stimulation site.

In some alternative examples, it may be desirable to decrease excitement of a stimulation site in order to treat obesity and/or type II diabetes. To facilitate decreased excitement of a stimulation site, the stimulation parameters may be adjusted such that the stimulator 120 applies a stimulation current having a relatively high frequency (e.g., greater than 100 Hz) to the stimulation site.

The stimulation parameters may also be adjusted such that the electrical and/or drug stimulation is applied to a stimulation site either intermittently or continuously. Intermittent stimulation may be more effective than continuous stimulation in some instances and vice versa.

It will be recognized that different stimuli may be applied to different stimulation sites to most effectively treat obesity and/or type II diabetes for a particular patient. Moreover, the stimulation parameters may be adjusted by the patient, a clinician, or other user of the stimulator 120 as best serves the particular patient being treated. The stimulation parameters may additionally or alternatively be automatically adjusted by the stimulator 120 in response to a sensed condition, as will be described below.

A number of exemplary stimulation parameters corresponding to a number of different stimulation sites will now be described. However, it will be recognized that the following descriptions are merely illustrative of the many different combinations of stimulation parameters and stimulation sites that may be used to treat obesity and/or type II diabetes.

In patients where the pituitary gland is stimulated to treat obesity and/or type II diabetes, the stimulation may be configured to modulate the release of ACTH (adrenocorticotropic hormone) by the pituitary gland. ACTH acts on the cells of the adrenal glands, stimulating them to produce glucocorticoids (e.g., cortisol). Cortisol promotes an increase in blood glucose. Hence, inhibiting the release of ACTH via inhibitory stimulation may lower the production of cortisol and/or other glucocorticoids and thereby lower the blood glucose level. This lowering of the blood glucose level may be useful in treating type II diabetes and/or obesity. Moreover, it has been discovered that the overproduction of cortisol can lead to overeating and/or increased fat production in the body. Hence, inhibition of the production of cortisol may additionally or alternatively be used to treat obesity and/or type II diabetes by preventing overeating and/or fat production.

In some alternative examples, excitatory stimulation may be applied to the pituitary gland to increase the release of ACTH in order to treat obesity and/or type II diabetes. An increase in ACTH production may be configured to cause stress to the patient and thereby promote weight loss. Hence, either inhibitory and/or excitatory stimulation may be used as may serve a particular application. In some embodiments, the particular stimulation parameters used to control the stimulation of the pituitary gland may be determined based on patient feedback and/or on a sensed indicator of obesity and/or type II diabetes, as described previously.

In patients where the anxiety and/or pleasure centers within the brain are stimulated to treat obesity and/or type II diabetes, the stimulation may be configured to prevent neural activity therein that usually occurs when the patient eats. It has been discovered that when people with overeating problems eat, neural activity in the pleasure center increases and neural activity in the anxiety center decreases. Hence, food has an addictive effect for many such patients. Thus, the stimulation parameters may be configured to inhibit neural activity within the pleasure center and/or increase neural activity within the anxiety center when a patient eats so that the patient does not feel the addictive effects. Without these addictive effects, the patient may be able to more easily form proper eating habits and thereby treat obesity and/or type II diabetes. In some embodiments, the particular stimulation parameters used to control the stimulation of the anxiety and/or pleasure centers may be determined based on patient feedback and/or on a sensed indicator of obesity and/or type II diabetes.

In some examples, the stimulator 120 is configured to communicate with and/or receive power from one or more devices located external to the patient. For example, an external battery charging system (EBCS) 201 may be provided to generate power that is used to recharge the power source 123 via any suitable communication link. Additional external devices including, but not limited to, a manufacturing and diagnostic system (MDS) 203, a hand held programmer (HHP) 205, and/or a clinician programming system (CPS) 207 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

If multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

Thus, one or more external devices may be provided to interact with the stimulator 120, and may be used to accomplish one or more of the following functions:

Function 1: If necessary, transmit electrical power to the stimulator 120 in order to power the stimulator 120 and/or recharge the power source 123.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional or alternative functions may include adjusting the stimulation parameters based on information sensed by the stimulator 120 or by other sensing devices.

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, or any other type of implantable device configured to deliver a stimulus to a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

The stimulator 120 of FIG. 2 may alternatively include a microstimulator. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
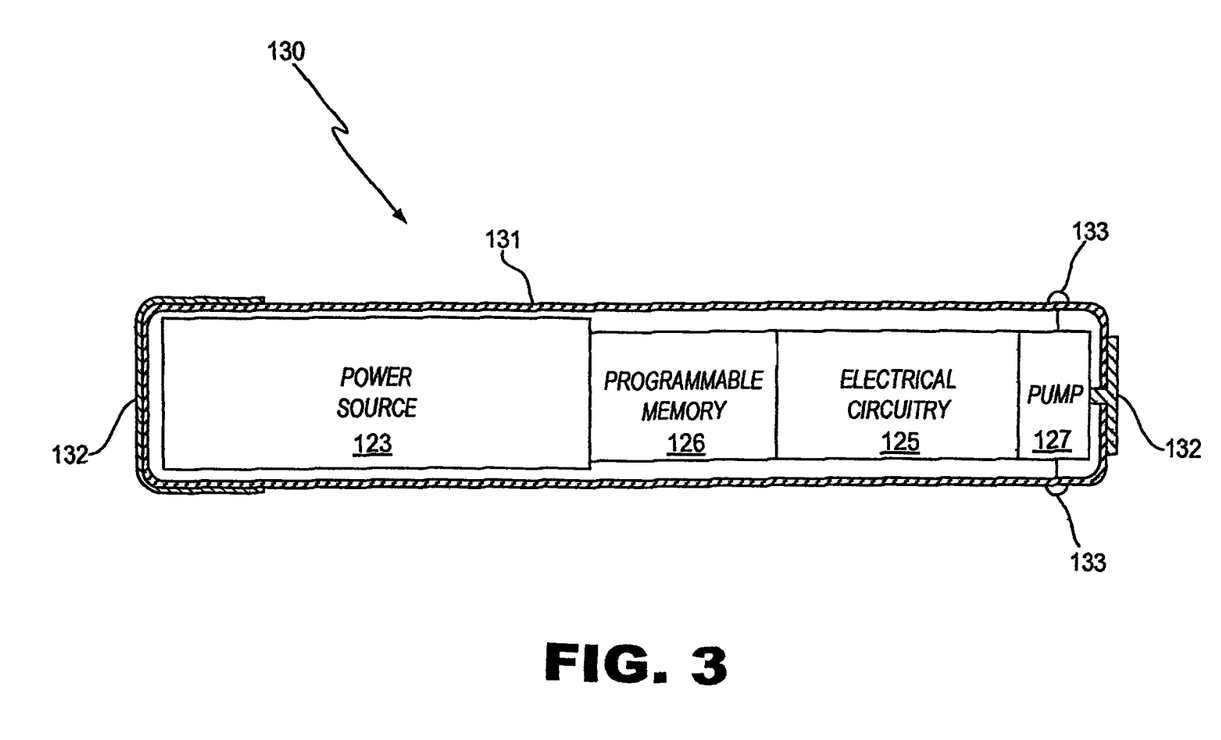
FIG. 3 illustrates an exemplary microstimulator according to principles described herein.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 123, the programmable memory 126, the electrical circuitry 125, and the pump 127 described in connection with FIG. 2. These components are housed within a capsule 131. The capsule 131 may be a thin, elongated cylinder or any other shape as best serves a particular application. The shape of the capsule 131 may be determined by the structure of the desired stimulation site and the method of implantation. In some examples, the microstimulator 130 may include two or more leadless electrodes 132 disposed on the outer surface thereof.

The external surfaces of the microstimulator 130 may advantageously be composed of biocompatible materials. For example, the capsule 131 may be made of glass, ceramic, metal, or any other material that provides a hermetic package that will exclude water vapor but permit passage of electromagnetic fields used to transmit data and/or power. The electrodes 132 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 133 configured to dispense one or more drugs directly at a stimulation site. Alternatively, one or more catheters may be coupled to the infusion outlets 133 to deliver the drug therapy to a treatment site some distance from the body of the microstimulator 130.

Figure 4A:
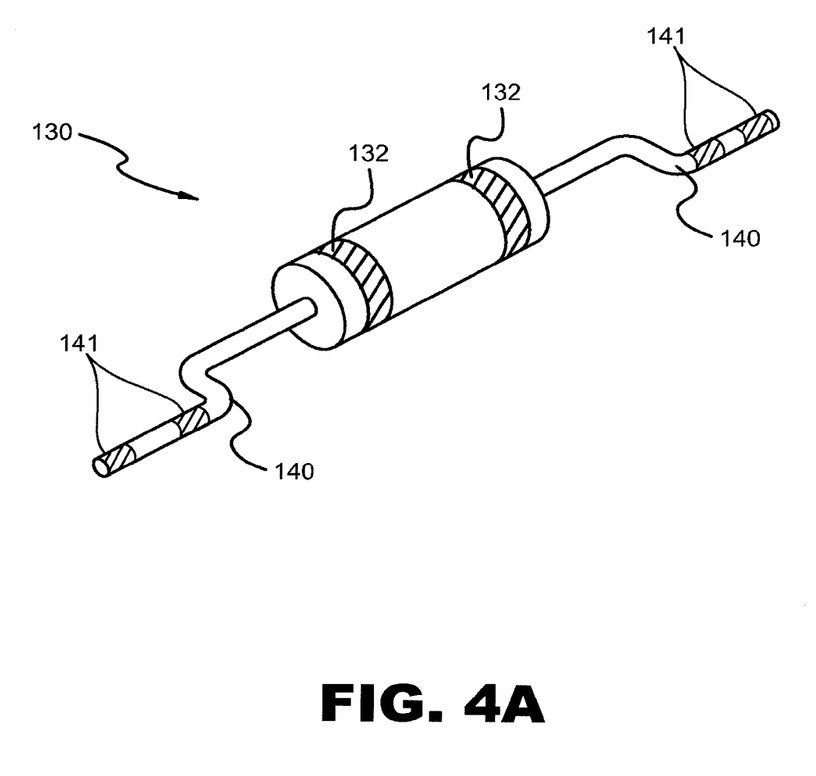
FIG. 4A shows an example of a microstimulator with one or more leads coupled thereto according to principles described herein.
Figure 4B:
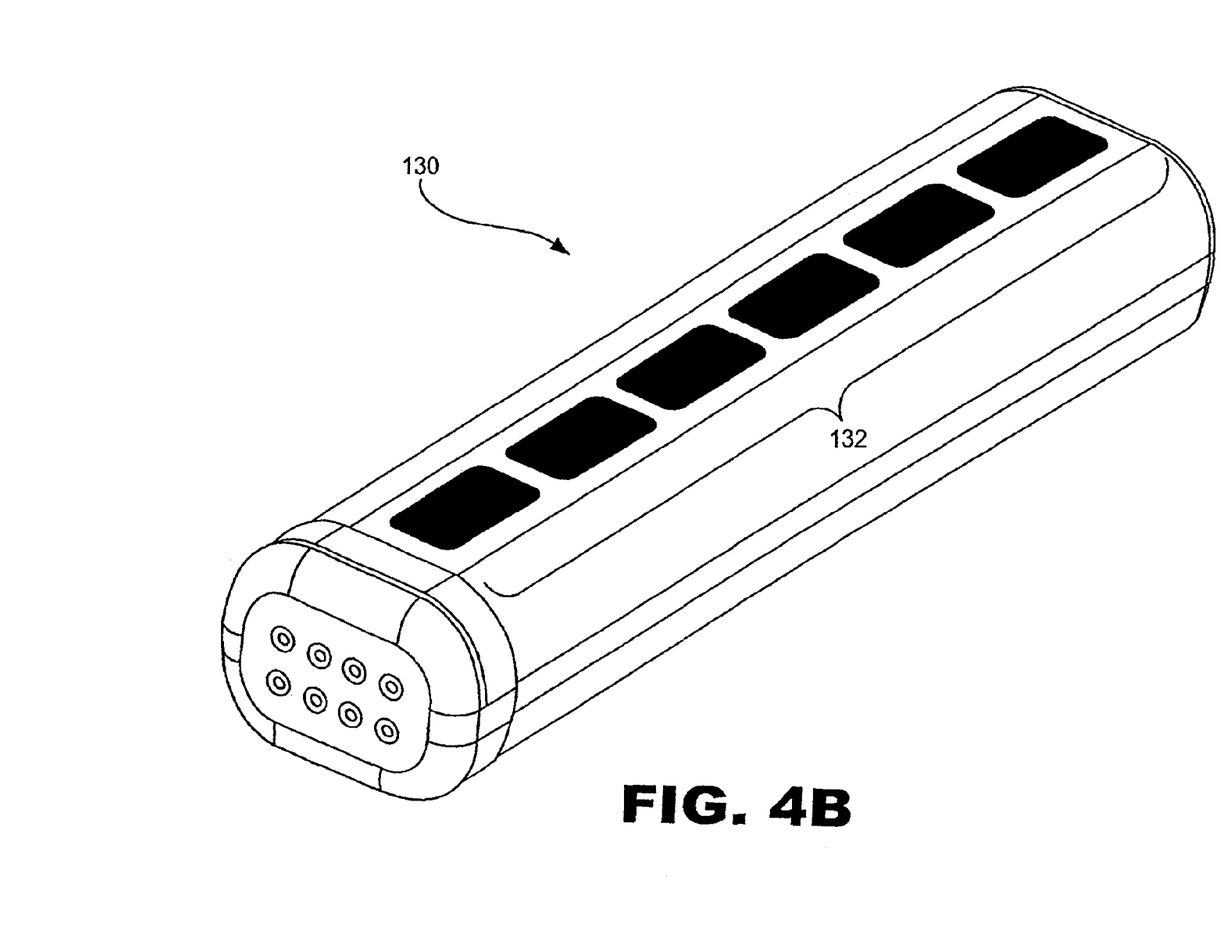
FIG. 4B shows an example of a microstimulator with a plurality of electrodes disposed on an outer surface thereof according to principles described herein.
Figure 4C:
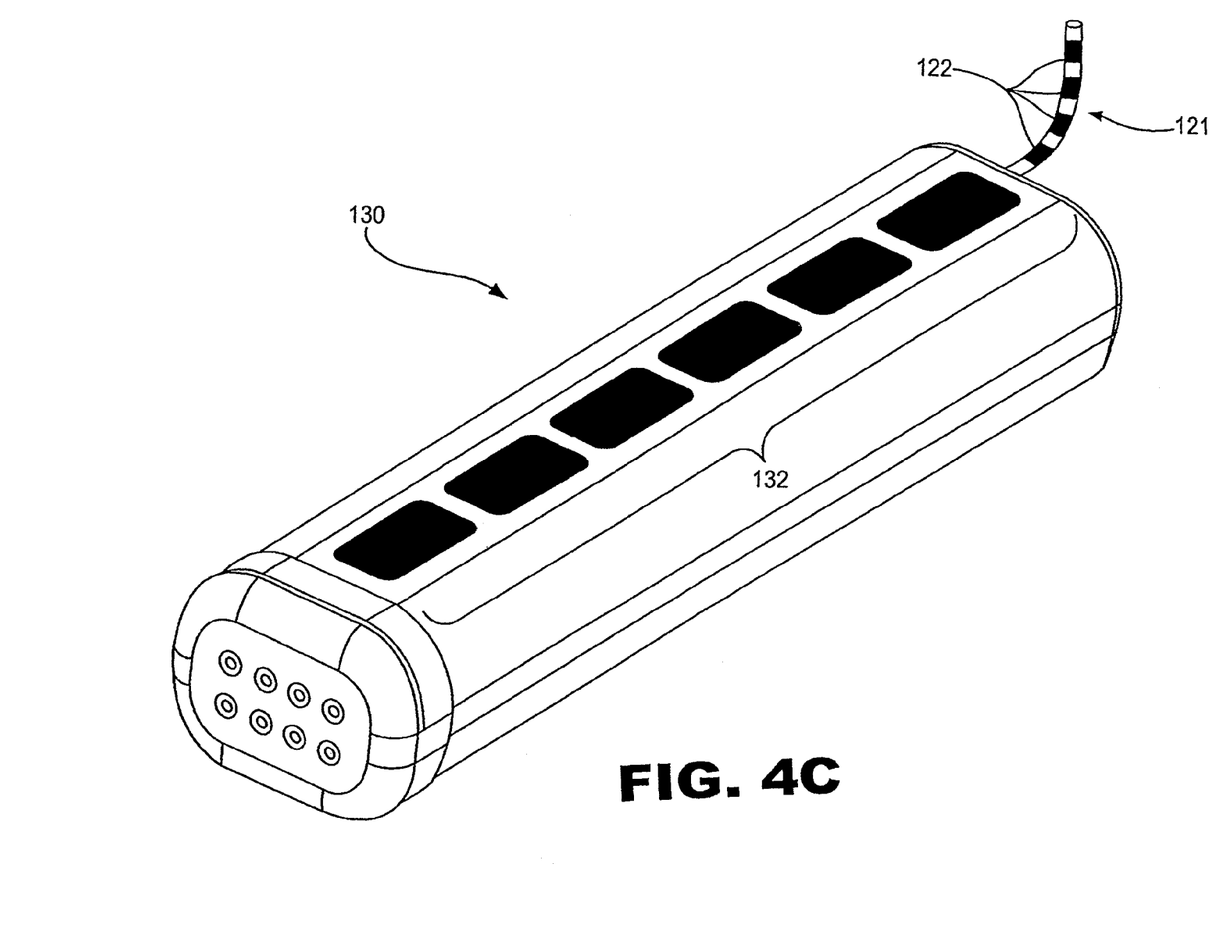
FIG. 4C shows the exemplary microstimulator of FIG. 4B coupled to a lead having a number of electrodes disposed thereon according to principles described herein.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 132 disposed on the outer surface thereof.

FIG. 4B illustrates an exemplary microstimulator 130 with a plurality of electrodes 132 disposed on an outer surface thereof. In some examples, any number of electrodes 132 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 132 and 122 may be selectively configured to serve as an anode or as a cathode.

Figure 5:
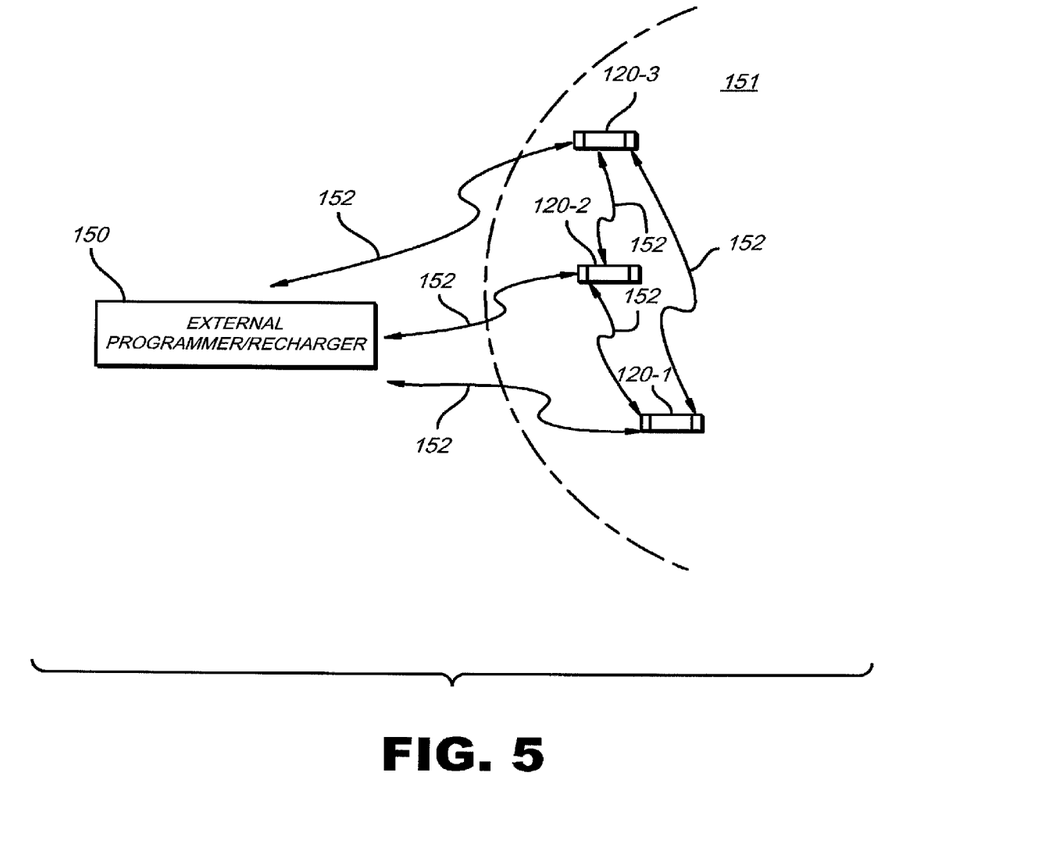
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the symptoms or causes of obesity and/or type II diabetes and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of obesity and/or type II diabetes, communicate or receive data regarding such indicators, and adjust stimulation parameters accordingly.

In order to determine the strength and/or duration of electrical stimulation and/or amount and/or type(s) of stimulating drug(s) required to effectively treat obesity and/or type II diabetes, various indicators of obesity and/or type II diabetes and/or a patient's response to treatment may be sensed or measured. To this end, the stimulator 120 may be in communication with and/or include a sensing device configured to sense any of a number of indicators related to obesity and/or type II diabetes.

The indicators that may be sensed include, but are not limited to, activity of gastric pacemaker cells, one or more scents, mastication rates, pressure against the stomach wall, stomach distension, stomach strain, naturally occurring electrical activity within the stomach (e.g., gastric slow waves), a rate of digestion of food within the stomach, and/or any other activity within the stomach. The indicators may additionally or alternatively include gastrointestinal hormone secretion levels, electrical activity of the brain (e.g., EEG), neurotransmitter levels, hormone levels, metabolic activity in the brain, blood flow rate in the head, neck or other areas of the body, medication levels within the patient, patient input (e.g., when a patient has the urge to eat, the patient can push a button on a remote control or other external unit to initiate the stimulation), temperature of tissue in the stimulation target region, physical activity level (e.g., based on accelerometer recordings), brain hyperexcitability, one or more indicators of collateral tissue stimulation, and/or detection of muscle tone (e.g., mechanical strain, pressure sensor, or electromyography (EMG)). In some examples, the stimulator 140 may be configured to adjust the stimulation parameters in a closed loop manner in response to one or more of these measurements.

By way of example, an exemplary method of treating obesity and/or type II diabetes may be carried out according to the following sequence of procedures. The steps listed below may be modified, reordered, and/or added to as best serve a particular application.

1. A stimulator 120 is implanted so that its electrodes 122 and/or infusion outlet 129 are in communication with a stimulation site within a patient (e.g., in communication with the pituitary gland). As used herein and in the appended claims, the term "in communication with" refers to the stimulator 120, stimulating electrodes 122, and/or infusion outlet 129 being adjacent to, in the general vicinity of, in close proximity to, directly next to, or directly on the stimulation site.

2. One or more stimulation parameters are configured to treat obesity and/or type II diabetes.

3. The stimulator 120 is programmed with the one or more stimulation parameters configured to treat obesity and/or type II diabetes. The stimulator 120 may then generate and apply at least one stimulus to the stimulation site in accordance with the stimulation parameters. The stimulus may include electrical stimulation, drug stimulation, gene infusion, chemical stimulation, thermal stimulation, electromagnetic stimulation, mechanical stimulation, and/or any other suitable stimulation.

4. When the patient desires to invoke stimulation, the patient sends a command to the stimulator 120 (e.g., via a remote control) such that the stimulator 120 delivers the prescribed stimulation to the stimulation site. For example, the stimulation may be activated by the patient when a particular incident of obesity and/or type II diabetes is detected. The stimulator 120 may alternatively or additionally be configured to apply the stimulation to the stimulation site in accordance with one or more pre-determined stimulation parameters and/or automatically apply the stimulation in response to sensed indicators of obesity and/or type II diabetes.

5. To cease or decrease stimulation, the patient may turn the stimulator 120 down or off (e.g., via a remote control).

6. Periodically, the power source 123 of the stimulator 120 is recharged, if necessary, in accordance with Function 1 described above.

In other examples, the treatment administered by the stimulator 120, i.e., drug therapy and/or electrical stimulation, may be automatic and not controlled or invoked by the patient. It will be recognized that the particular stimulation methods and parameters may vary as best serves a particular application.

Figure 6:
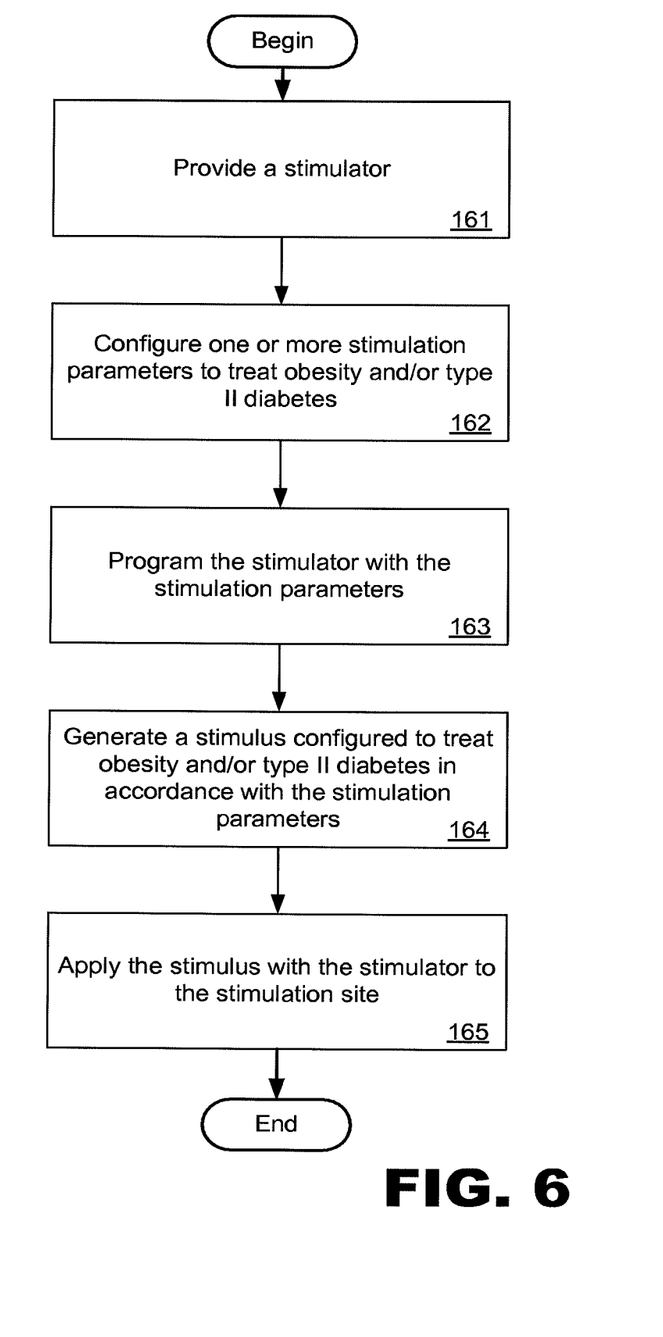
FIG. 6 is a flow chart illustrating an exemplary method of treating obesity and/or type II diabetes according to principles described herein.

FIG. 6 shows a flowchart of an exemplary method of treating obesity and/or type II diabetes, according to the principles that have been described in more detail above. While FIG. 6 illustrates exemplary steps according to one embodiment, other embodiments may omit, add to, reorder, and/or modify any of the steps shown in FIG. 6.

In step 161, a stimulator is provided. In step 162, one or more stimulation parameters are configured to treat obesity and/or type II diabetes. In step 163, the stimulator is programmed with the stimulator parameters. In step 164, a stimulus configured to treat obesity and/or type II diabetes in accordance with the stimulation parameters is generated. In step 165, the stimulus is applied with the stimulator to the stimulation site.

The stimulator 120 may be implanted within a patient using any suitable surgical procedure such as, but not limited to, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501,703; 6,487,446; and 6,516,227. Exemplary methods of implanting a deep brain stimulator, for example, are described in U.S. Pat. Nos. 5,938,688; 6,016,449; and 6,539,263. All of these listed patents are incorporated herein by reference in their respective entireties.

Figure 7:
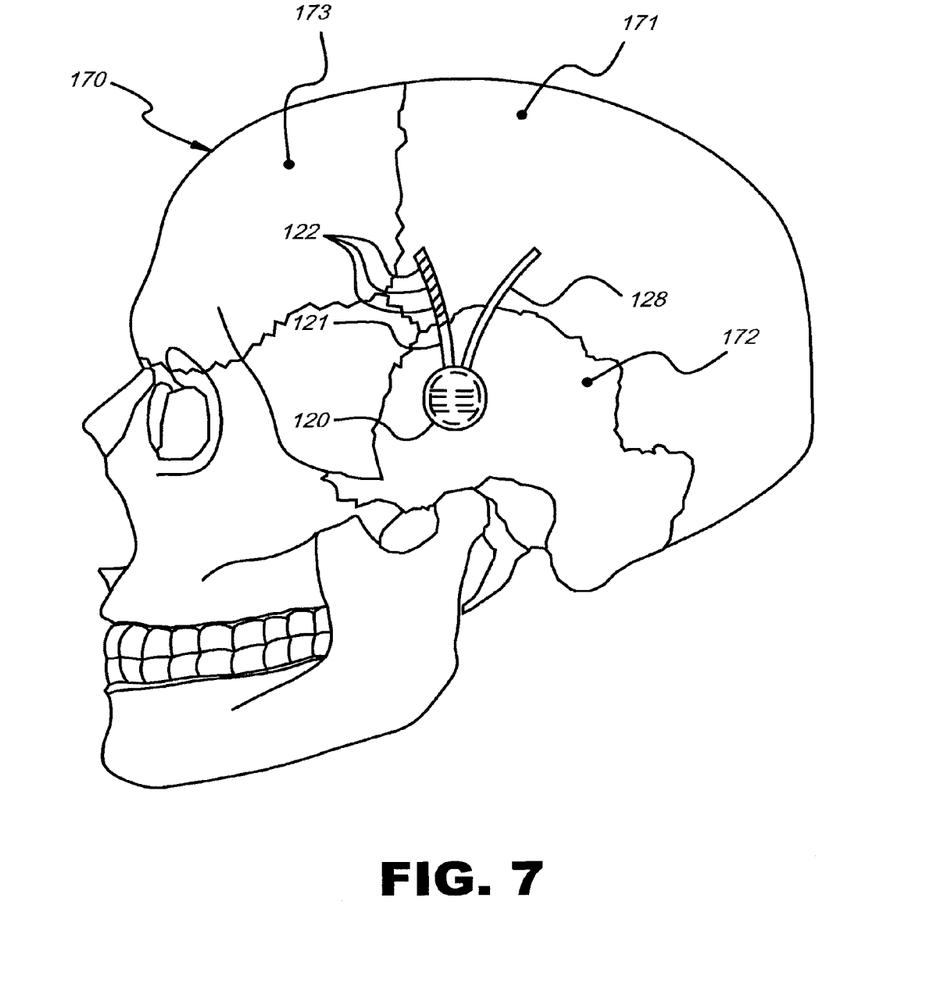
FIG. 7 illustrates a stimulator that has been implanted beneath the scalp of a patient to stimulate a stimulation site within the brain according to principles described herein.

To illustrate, the stimulator 120 may be implanted beneath the scalp of a patient to stimulate a stimulation site within the brain. For example, as shown in FIG. 7, the stimulator 120 may be implanted in a surgically-created shallow depression or opening in the skull 170. The depression may be made in the parietal bone 171, temporal bone 172, frontal bone 173, or any other bone within the skull 170 as may serve a particular application. The stimulator 120 may conform to the profile of surrounding tissue(s) and/or bone(s), thereby minimizing the pressure applied to the skin or scalp. Additionally or alternatively, the stimulator 120 may be implanted in a subdural space over any of the lobes of the brain, in a sinus cavity, or in an intracerebral ventricle.

In some embodiments, as shown in FIG. 7, a lead 121 and/or catheter 123 run subcutaneously to an opening in the skull 170 and pass through the opening such that it is in communication with a stimulation site (e.g., the pituitary gland) in the brain. Alternatively, the stimulator 120 is leadless and is configured to generate a stimulus that passes through the skull. In this manner, a stimulation site within the brain may be stimulated without having to physically invade the brain itself.

Figure 8:
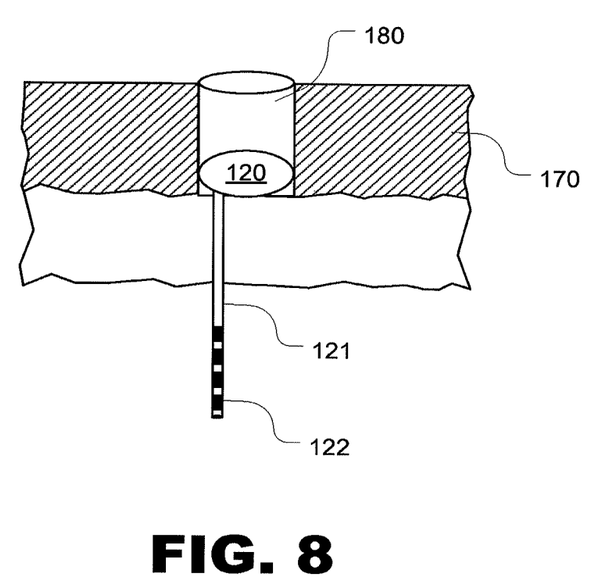
FIG. 8 is cross-sectional view of a stimulator implanted within a hole created in the skull of a patient according to principles described herein.

Alternatively, as shown in the cross-sectional view of FIG. 8, the stimulator 120 may be implanted within the lumen of a hole 180 created in the skull 170 and configured to apply a stimulus at a stimulation site within the brain (e.g., the pituitary gland). The hole 180 may be a burr hole, for example, and may be created with a surgical drill or any other suitable device. The hole 180 extends at least partially into the skull 170. The stimulator 120 may be placed within the lumen of the hole 180 and coupled to the walls of the hole 180 using an adhesive, suture, or any other fastening device. Once the stimulator 120 has been implanted, the hole 180 may be covered by an appropriately sized cap (not shown).

As shown in FIG. 8, a lead 121 may be coupled to the stimulator 120 with the distal end of the lead 121 being routed to a particular location in communication with a stimulation site within the brain (e.g., the pituitary gland). A distal potion of the lead 121 may include one or more electrodes 122 configured to deliver an electrical stimulation current to the stimulation site. A catheter (not shown) may additionally or alternatively be coupled to the stimulator 120 and routed to the stimulation site so as to deliver one or more drugs at the stimulation site.

In some examples wherein the stimulation site is the pituitary gland, the stimulator 120 may be implanted using a trans-sphenoidal approach. In other words, the stimulator 120 and/or lead 121 may be implanted through the sphenoid sinus just posterior to the nasal cavity. In this manner, passage of the stimulator 120 and/or lead 121 through the tissue of the brain may be avoided.

It will be recognized that the implant locations of the stimulator 120 described herein are merely illustrative and that the stimulator 120 may additionally or alternatively be implanted in any other suitable location within the body.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with at least one of obesity and type II diabetes, comprising:
    applying a stimulus to a pituitary gland within the patient in accordance with one or more stimulation parameters, thereby treating the at least one of obesity and type II diabetes;
    sensing at least one indicator related to one or more effects of the at least one of obesity and type II diabetes, wherein the sensed at least one indicator comprise one or more of an activity of gastric pacemaker cells, a scent, a mastication rate, pressure against the stomach wall, stomach distension, stomach strain, naturally occurring electrical activity within the stomach, a rate of digestion of food within the stomach, tissue temperature, and muscle tone; and
    adjusting the one or more stimulation parameters based on the sensed at least one indicator.

2. The method of claim 1, wherein the applied stimulus modulates one or more hormones produced by the pituitary gland.

3. The method of claim 2, wherein the one or more hormones produced by the pituitary gland comprises an adrenocorticotropic hormone.

4. The method of claim 3, wherein the applied stimulus inhibits production of the adrenocorticotropic hormone.

5. The method of claim 3, wherein the applied stimulus increases production of the adrenocorticotropic hormone.

6. The method of claim 1, wherein the stimulus comprises an electrical current.

7. The method of claim 1, wherein the stimulus comprises one or more drugs.

8. The method of claim 1, wherein the at least one indicator comprises an activity of gastric pacemaker cells.

9. The method of claim 1, wherein the at least one indicator comprises a scent.

10. The method of claim 1, wherein the at least one indicator comprises a mastication rate.

11. The method of claim 1, wherein the at least one indicator comprises a pressure against the stomach wall.

12. The method of claim 1, wherein the at least one indicator comprises a stomach distension or a stomach strain.

13. The method of claim 1, wherein the at least one indicator comprises a naturally occurring electrical activity within the stomach.

14. The method of claim 1, wherein the at least one indicator comprises a rate of digestion of food within the stomach.

15. The method of claim 1, wherein the at least one indicator comprises tissue temperature.

16. The method of claim 1, wherein the at least one indicator comprises muscle tone.

\* \* \* \* \*